Aug. 24, 1943. H. R. MOSNAT Plant Pat. 598
CHRYSANTHEMUM PLANT
Filed Feb. 6, 1943
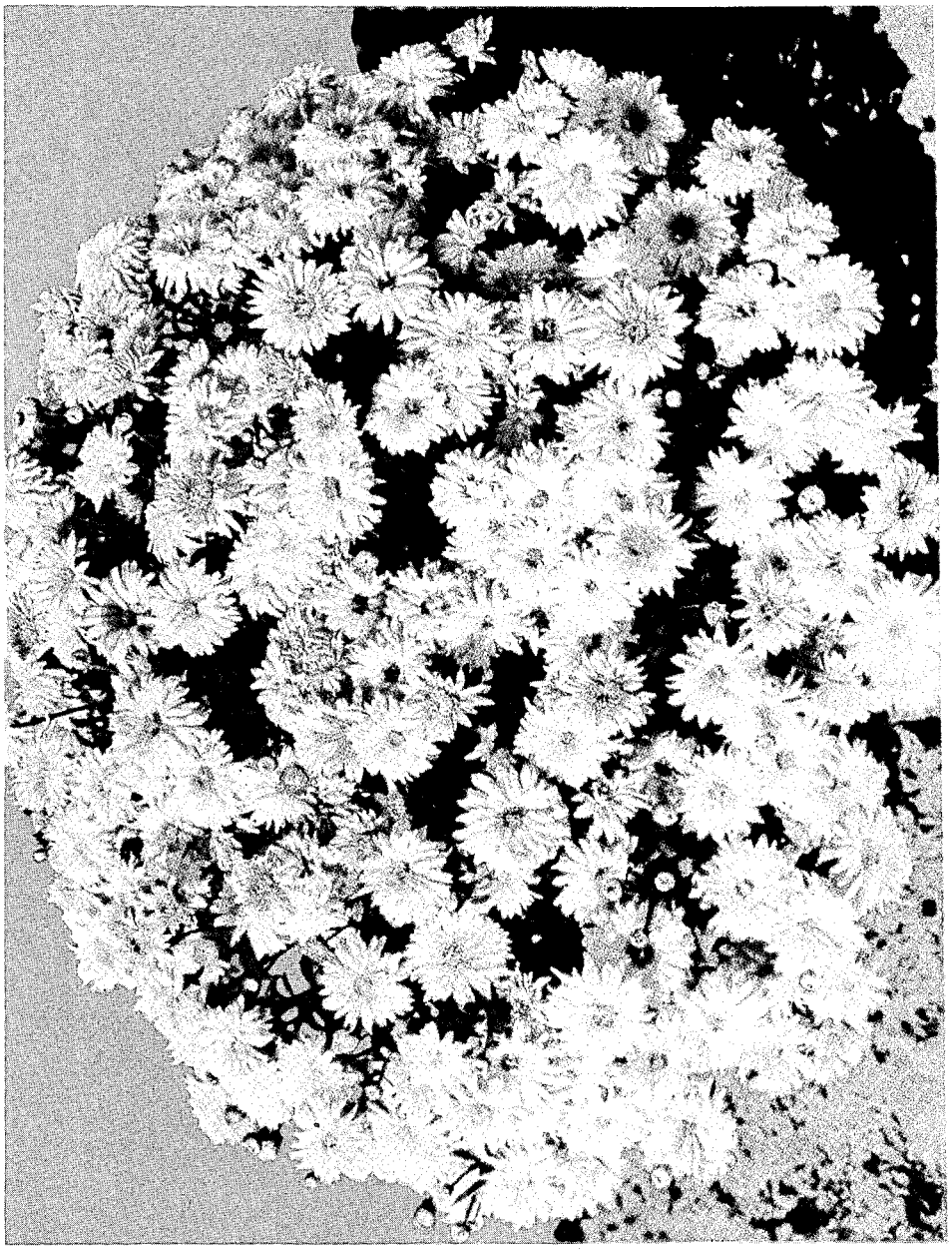
Inventor:
H. R. Mosnat
By: Robb & Robb
Attorneys Patented Aug. 24, 1943

Plant Pat. 598

UNITED STATES PATENT OFFICE

598

CHRYSANTHEMUM PLANT

Hugo Roy Mosnat, Belle Plaine, Iowa, assignor to The R. M. Kellogg Company, Three Rivers, Mich.

Application February 6, 1943, Serial No. 475,009

1 Claim. (Cl. 47—60)

My present invention consists of a new and distinct variety of chrysanthemum plant.

The plant of this invention is unusually compact for a chrysanthemum plant, but not as much of a bush or as low as the common cushion varieties of mums. It does not break down and sprawl as to plant structure, and therefore is a new type in reference to this particular phase of its growth since it is very advantageous for landscaping. The height of a fully grown plant of my new variety is about twenty inches.

The flowers of my new variety of chrysanthemum last several weeks on the plant and are especially characterized by the quality of not fading for a long tme, even when exposed to the most intense actinic rays of sunlight.

Another novel characteristic of my new chrysanthemum lies in the size of its flowers, which are particularly large for an outdoor growing mum, being about 2½" in diameter when fully maturing. The flowers likewise are of a very double and somewhat pom-pom type, especially when the are not too old. In explanation of the foregoing, it is notable that the blossoms of my chrysanthemum are high in the center and flatten somewhat as they approach maturity or age.

For a full recognition of the new qualities and other characteristics of my new variety of plant reference is made to the accompanying color drawing illustrative of the plant in blooming condition.

A detail description of the plant is as follows:

Type: Seedling.
Breeding: Seedling.
Parentage:
*Seed parent.*—Pink Cushion.
*Pollen parent.*—Korean hybrid.
Classification:
*Botanical.*—"Chrysanthemum Hortorum."
Propagation.—Holds its distinguishing characteristics through succeeding propagations by cuttings, grafting, and budding.

*Flower*

Locality where grown: Belle Plaine, Iowa.
Blooming habit: Begins to bloom early in July, or even last of June, being very early, and keeps on until frost.
Bud: Not affected by wet or hot weather.
*Size.*—Large.
*Color.*—Cadmium Orange (Horticultural Chart 8/1). Open flower: Lemon Yellow (Horticultural Chart 4/1).
*Sepals.*—Smooth edge; curl back.
Bloom:
Size.—Large, average size when fully expanded, 2½".
*Borne.*—Singly.
*Stems.*—Long, strong.
Petals:
*Texture.*—Thick.
*Not affected by cold weather.*
*Appearance.*—Satiny both inside and outside.
*Petaloids in center.*—Many.
*Persistence.*—Hang on and dry.
*Fragrance.*—None.
*Scent.*—Chrysanthemum.
*Lastingness on plant.*—Very long.
*Lastingness as cut flower.*—Very long.
Genital organs:
*Stamens, anthers.*—Many.
*Stamens, filaments.*—Lemon yellow in color.
*Pollen.*—Lemon yellow.

*Plant*

Form: Bush.
Growth: Vigorous.
Foliage:
*Size.*—Medium.
*Quantity.*—Normal.
*Color.*—Normal green for new and old foliage.
*Shape.*—Oval, pointed.
*Texture.*—Smooth on upper side and rough on under side.
*Ribs and veins.*—Ordinary.
*Edge.*—Serrated (saw toothed).
*Serration.*—Deep.
*Leaf stem.*—Green in color and smooth under side.

As indicated in the foregoing, my new chrysanthemum plant has been obtained by crossing the variety Pink Cushion (Amelia) with Korean hybrids, obtaining its dwarf type of plant from the Cushion parent and its size and doubleness and color from the Korean parent. The new variety resulting is much hardier than Korean mums and even hardier than cushion mums, and in addition the following primary characteristics may be summarized:

(*a*) The flowers of my variety of chrysanthemum when open remain on the plant for several weeks and do not fade. The blossoms are, when open, Canary Yellow.

(*b*) The flowers are large as respects outdoor mums, being about 2½" in diameter.

(*c*) The chrysanthemum of my new variety is characterized by its quality of not fading for a long time, even right out in the intense actinic rays of sunlight.

(*d*) The blooms on my new variety of chrysanthemum plant appear very early in July or even the last of June in latitude 254 miles due west of Englewood, Chicago, Illinois, and the buds and flowers are borne above the foliage.

(*e*) My new variety of chrysanthemum is much hardier than Korean mums and even hardier than cushion mums, and the plant continues in good bloom for a long period of time, until hard, killing frosts.

(*f*) My plant reproduces itself well, being a free producer of rhizomes (root sprouts), the plant producing up to 75 or 80 each.

(*g*) The stem of my plant are long enough for the plant to be useful for cutting.

(*h*) My plant is a profuse bloomer.

(*i*) The color of my new plant is unique as it is yellow with enough orange to make it attractive. The foregoing is doubtless the reason for the non-fading quality of the flower.

I claim:

The new and distinct variety of chrysanthemum plant obtained from crossing the variety Pink Cushion with Korean Hybrids, characterized as to novelty by its production of especially large flowers, the non-fading quality of the flowers even when subjected to intense sunlight, its early blooming characteristic, its greater hardiness than Korean and Cushion mums, its long blooming period, its novel color, and its free production of large amounts of rhizomes, substantially as shown and described.

HUGO ROY MOSNAT.